US005935957A

United States Patent [19]

Diana et al.

[11] Patent Number: 5,935,957

[45] Date of Patent: Aug. 10, 1999

[54] COMPOUNDS, COMPOSITIONS AND METHODS FOR TREATING INFLUENZA

[75] Inventors: Guy D. Diana, Pottstown; Thomas R. Bailey, Phoenixville; Theodore J. Nitz, Pottstown; Dorothy C. Young, Collegeville; William P. Gorczyca, Pottstown, all of Pa.

[73] Assignee: Viropharma Incorporated, Exton, Pa.

[21] Appl. No.: 09/082,656

[22] Filed: May 21, 1998

Related U.S. Application Data

[63] Continuation of application No. 08/858,649, May 19, 1997, which is a continuation-in-part of application No. 08/681,289, Jul. 22, 1996, abandoned.

[51] Int. Cl.[6] .......................... A61K 31/50; A61K 43/60

[52] U.S. Cl. .......................... 514/247; 514/253; 514/254

[58] Field of Search .................................. 514/247, 253, 514/254

[56] References Cited

U.S. PATENT DOCUMENTS

| | | | |
|---|---|---|---|
| 3,152,180 | 10/1964 | Haaf | 260/51 |
| 3,352,912 | 11/1967 | Prichard | 260/563 |
| 3,483,254 | 12/1969 | Shen et al. | 260/563 |
| 3,496,228 | 2/1970 | Hoover | 260/563 |
| 3,534,084 | 10/1970 | Narayanan et al. | 260/490 |
| 3,538,160 | 11/1970 | Dunn et al. | 260/563 |
| 3,592,934 | 7/1971 | Prichard | 424/325 |
| 5,684,024 | 11/1997 | Diana et al. | 514/364 |
| 5,821,243 | 10/1998 | Diana et al. | 514/247 |

OTHER PUBLICATIONS

H. Fraenkel–Conrat and A. Steinschneider, "Stepwise Degradation of RNA: Periodate Followed by Aniline Cleavage," *Methods of Enzymology*, 12B: 243–246 (1967).

S.J. Plotch, M. Bouloy and R.M. Krug, "Transfer of 5'–Terminal Cap of Globin mRNA to Influenza Viral Complementary RNA during Transcription in Vitro," Proc. Natl. Acad. Sci. USA, 76: 1618–1622 (1979).

R. Pauwels, J. Balzarini, M. Baba, R. Snoeck, D. Schols, P. Herdewijn, J. Desmyter and E. DeClerq, "Rapid and automated tetrazolium–based colorimetric assay for the detection of anti–HIV compounds", *J. Virol. Methods*, 20: 309–321 (1988).

G.A. Russell and P. Bruni, "Aliphatic Semidiones—XI: Radical Anions Derived by Reduction of 1–Phenyl–3–methyl–2–pyrazoline–4,5–dione, 1,2,–diphenylpyrazolidene–3,4,5–trione and 1,1'–Diphenyl–3, 3'–di–methyl–4,4'–bis–2–pyrazoline–5–5'–dione (Pyrazole–blue)", *Tetrahedron*, 26: 3449–3456 (1970).

*Primary Examiner*—Mukund J. Shah
*Assistant Examiner*—Bruck Kifle
*Attorney, Agent, or Firm*—Dann, Dorfman, Herrell & Skillman

[57] ABSTRACT

Compounds of the formula:

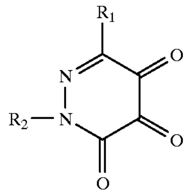

wherein R1 represents a lower alkyl (C1–C6) substituent which may be straight or branched; R2 represents an aryl substituent of the formula:

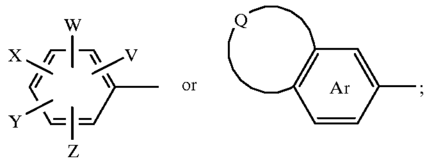

and Q, V, W, X, Y and Z are as set forth in the accompanying specification, are useful in prophylaxis of influenza virus infection.

5 Claims, No Drawings

COMPOUNDS, COMPOSITIONS AND METHODS FOR TREATING INFLUENZA

This is a continuation of co-pending U.S. application Ser. No. 08/858,649, filed May 19, 1997, which is a continuation-in-part of U.S. application Ser. No. 08/681,289, filed Jul. 22, 1996 (now abandoned).

FIELD OF THE INVENTION

The present invention relates to compounds, compositions and methods for the treatment of influenza infection. In particular, the present invention relates to novel pyridazine derivatives, pharmaceutical compositions containing such derivatives and their use in treating influenza infection and other viral diseases.

BACKGROUND OF THE INVENTION

There are three known influenza-type viruses which affect human beings: Influenza A, B and C. Influenza A viruses have been isolated from many animal species in addition to humans, while the influenza B and C viruses infect mainly humans. The influenza viruses are enveloped viruses containing negative single-stranded RNA's which are segmented and encapsidated. The influenza virus envelope is characterized by the presence of two surface glycoproteins: hemagglutinin and neuraminidase. The influenza A and B virions are pleomorphic and are usually 80–120 nm in diameter. The influenza C virion has many distinctive properties and is thus distinguished from the closely related A and B virions. Infection with influenza A or B often can cause a highly contagious, acute respiratory illness.

Influenza viruses have a major impact on morbidity leading to increases in hospitalization and in visits to health care providers. High rates of hospitalization are observed for patients over 65 years of age and also for children less than 5 years of age. Influenza virus is also unique among respiratory viruses in being a cause of excess mortality. Furthermore, the spread of influenza virus through a population can result in epidemics which have considerable economic impact. For example, high rates of mortality were observed due to influenza infection during the influenza epidemics of 1957, 1968 and 1977. *Fields Virology,* Second Edition, Volume 1, pp. 1075–1152 (1990).

There are relatively few known compounds that have significant anti-viral activity against influenza viruses. Two of these, amantadine and rimantadine are approved in the United States for the treatment of influenza virus disease. Both compounds are most effective when used prophylactically and influenza viruses develop resistance to both compounds rapidly. See U.S. Pat. No. 3,152,180 and 3,352,912. Other compounds reported to have activity against influenza viruses are disclosed in U.S. Pat. Nos. 3,483,254, 3,496,228, 3,538,160, 3,534,084 and 3,592,934.

Insofar as is known, pyridazine derivatives have not been previously reported as being useful for the treatment of influenza infection.

SUMMARY OF THE INVENTION

In accordance with one aspect, the present invention provides compounds, including isomeric forms, of the following structure:

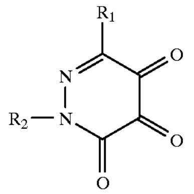

wherein $R_1$ represents a lower alkyl ($C_1$–$C_6$) substituent which may be straight or branched; $R_2$ represents an aryl substituent of the formula:

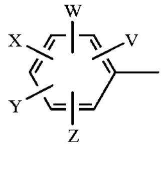 or 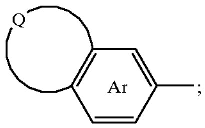 ;

V represents a substituent selected from the group consisting of $COOR_3$, $CONR_4R_5$, $SO_2NR_6R_7$ and

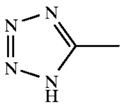 , 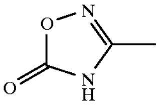 ,

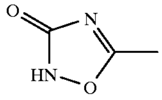 , 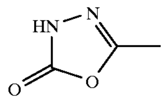 ;

W, X, Y and Z represent the same or different substituents selected from the group consisting of H, alkyl, halogen, $CF_3$, alkoxy, COOH, alkylthio, alkylsulfinyl, alkylsulfonyl COOR' and CONR"R'"; Q and the carbon atoms to which it is attached represent a heterocyclic ring selected from the group consisting of

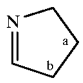 , 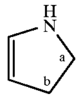 , 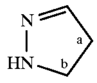 ,

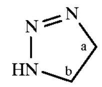 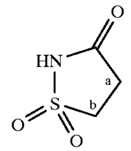 , 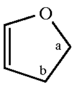 ,

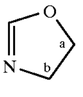 , 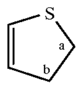 and 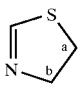 ;

wherein the bond between positions a, b of said heterocyclic ring forms a common bond with aromatic ring (Ar); $R_3$ and R' are the same or different and represent H or an alkyl ($C_1$–$C_6$) substituent; $R_4$, $R_5$, $R_6$, $R_7$, R" and R'" are the same or different and represent H, an alkyl substituent, an aryl substituent, an aralkyl substituent, a heterocyclic substituent, a heterocyclicalkyl substituent, or a carboxyalkyl substituent, said aryl substituent and the aryl moiety of said aralkyl substituent having the formula:

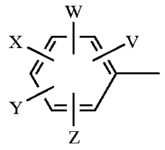

or

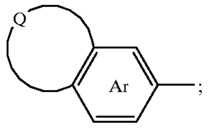

wherein Q, V, W, X, Y and Z are as previously defined, said heterocylic substituent or the heterocylic moiety of said heterocyclicalkyl substituent having the formula

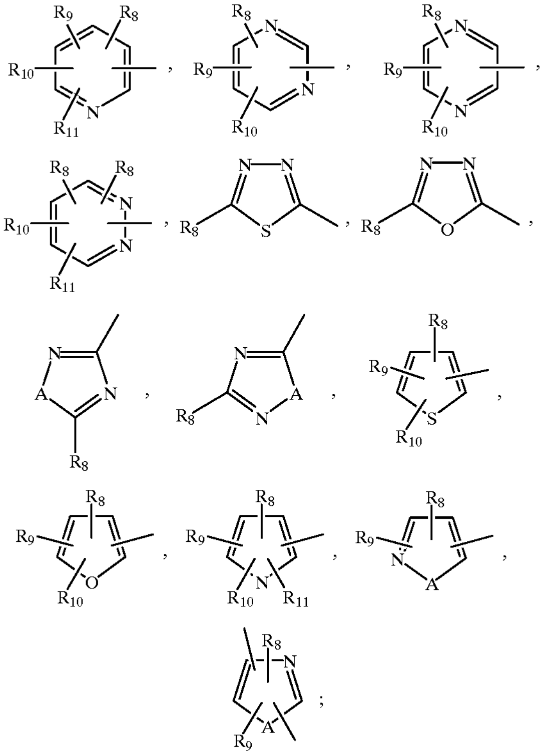

wherein A is selected from the group consisting of carbon, nitrogen, sulfur or oxygen, and $R_8$, $R_9$, $R_{10}$, $R_{11}$ are the same or different and represent H, alkyl, halogen, $CF_3$, alkoxy, alkylthio, OH, alkylamino, dialkylamino, COOH, $CONH_2$ and $SO_2NH_2$, and the isomers and pharmaceutically acceptable salts of said compound.

Included within the invention also are the pharmaceutically acceptable salts of the above compounds.

According to still another aspect, the present invention provides pharmaceutical compositions comprising one or more of the above-described pyridazine derivatives in combination with a pharmaceutically acceptable carrier medium.

In accordance with yet another aspect, the present invention provides a method for treating viral influenza infections in mammalian hosts by administering an effective amount of the compounds of the invention to a patient susceptible to influenza infection or suffering from such an infection.

DETAILED DESCRIPTION OF THE INVENTION

The compounds of the invention can be conveniently prepared from known starting materials and specific embodiments of anti-influenza compounds within the scope of the invention are exemplified below.

In vitro studies demonstrating the usefulness of the compounds of the invention as anti-viral agents against the influenza virus have been performed. Anti-viral activity was measured on the basis of inhibition of influenza virus transcriptase, reduction in plaque formation by the influenza virus and reduction in cleavage of cap 1 RNA by the influenza virus. In addition, the effect of the anti-influenza compounds on cell growth was measured using a tetrazolium salt (MTT) method. Finally, drug acute tolerance was measured using studies on mice. These biological studies of the anti-viral activity of the compounds of the invention are described in the examples that follow.

Among the particularly preferred embodiments of the invention are compounds, including isomeric forms, having the formula:

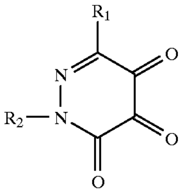

wherein $R_1$ represents $CH_3$; $R_2$ represents

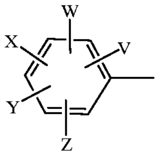

V represents a substituent selected from the group consisting of $COOH_3$, $SO_2NR_4R_5$ and

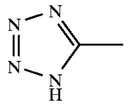

$R_4$ and $R_5$ are the same or different and represent H, acetyl, methyl, substituted or unsubstituted phenyl, or substituted or unsubstituted pyridyl, said phenyl and said pyridyl substituents being selected from those consisting of alkyl, alkoxy, hydroxy, carboxy and halogen groups; W represents a substituent selected from the group consisting of H, $CH_3$ or Cl; X, Y and Z represent H; and the pharmaceutically acceptable salts of said compounds.

Also preferred are compounds, including isomeric forms, having the formula:

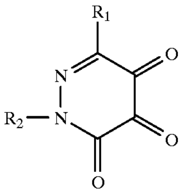

wherein $R_1$ represents $CH_3$; $R_2$ represents

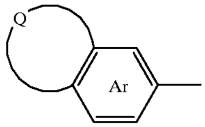

Q and the carbon atoms to which it is attached represent a heterocyclic ring selected from the group consisting of

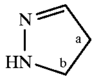 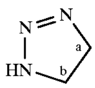 and 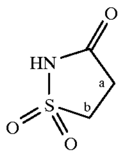

wherein the bond between positions a, b of said heterocyclic ring forms a common bond with aromatic ring (Ar); and the isomers and pharmaceutically acceptable salts of said compound.

The term "alkyl" as used herein refers to aliphatic hydrocarbon radicals of one to six carbon atoms in length. Similarly, the term "alkyl", or any variation thereof, used in combination form to name substituents, such as alkoxy (—O—alkyl), alkylthio (—S—alkyl), alkylamino (—NH—alkyl), alkylsulfonyl (—$S(O)_2$—alkyl), carboxyalkyl (—alkyl—COOH), or the like, also refers to aliphatic hydrocarbon radicals of one to six carbon atoms in length, and preferably of one to four carbon atoms in length.

Isomers of the compound of Formula I, above, that are within the scope of the invention include, without limitation, tautomeric forms of such compound.

As previously noted, the compounds of Formula I, above, including their pharmaceutically acceptable salts, exhibit antiviral activity against influenza virus.

The compounds of the invention can form salts with inorganic and organic bases, including, for example, alkali metal salts, such as Na or K salts, alkaline earth metal salts, such as Ca or Mg salts, ammonium, substituted ammonium and other amine salts such as morpholine, piperidine or pyridine salts.

The pharmaceutically acceptable salts of the compounds of formula I are prepared following procedures which are familiar to those skilled in the art.

The antiviral pharmaceutical compositions of the present invention comprise one or more of the compounds of formula I above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences,* Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.1% and not more than 50% by weight based on the total weight of the composition, including carrier medium and/or auxiliary agent(s). Preferably, the proportion of active agent varies between 0.1 to 5% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers for medicaments may all be suitable as carrier media.

The compounds of the invention may be administered using any amount and any route of administration effective for attenuating infectivity of the influenza virus. Thus, the expression "amount effective to attenuate infectivity of influenza virus", as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent, its mode of administration, and the like. The anti-influenza compounds of the invention are preferably formulated in dosage unit form for ease of administration and uniformity of dosage. The expression "dosage unit form" as used herein refers to a physically discrete unit of anti-viral agent appropriate for the patient to be treated. Each dosage should contain the quantity of active material calculated to produce the desired therapeutic effect either as such, or in association with the selected pharmaceutical carrier medium. Typically, the antiviral compounds of the invention will be administered in dosage units containing from about 5 mg to about 500 mg of the anti-viral agent with a range of about 0.1 mg to about 50 mg being preferred.

The compounds of the invention may be administered orally, parenterally, such as by intramuscular injection, intraperitoneal injection, aerosol, intravenous infusion or the like, depending on the severity of the infection being treated. The compounds of the invention may be administered orally or parenterally at dosage levels of about 0.1 mg/kg to about 50 mg/kg and preferably from about 2 mg/kg to about 25 mg/kg, of patient body weight per day, one or more times a day, to obtain the desired therapeutic effect.

Although the pyridazine derivatives described herein can be administered to any patient which is susceptible to influenza infection, the compounds are intended for the treatment of mammalian hosts, and especially humans.

The compounds of the invention will typically be administered from 1 to 3 times a day so as to deliver the above-mentioned daily dosage. However, the exact regimen for administration of the compounds and compositions described herein will necessarily be dependent on the needs of the individual patient being treated, the type of treatment administered and the judgment of the attending physician.

In view of the inhibitory effect on influenza virus transcriptase produced by the compounds of the invention, it is anticipated that these compounds will be useful not only for therapeutic treatment of infection, but for influenza viral prophylaxis, as well. The above-noted dosages will be essentially the same whether for treatment or prophylaxis of influenza infection.

The following examples are provided to describe the invention in further detail. These examples, which set forth the best mode presently contemplated for carrying out the invention, are intended to illustrate and not to limit the invention.

Examples 1 to 10 illustrate the chemical synthesis of ten compounds which are considered representative embodiments of the invention. In the examples below in which acidification was carried out, the intermediates or the compounds of the invention were acidified to pH 3.0. The expression "concentrated hydrochloric acid", as used in the examples, refers to 3N HCl. Also in the examples below, "excess triethylamine" means 0.5 ml triethylamine when less than one gram of compound is being extracted or purified, and "excess triethylamine" means 1 ml triethylamine when 1–1.5 grams of compound is being extracted or purified, based on the calculated theoretical yield.

EXAMPLE 1

Preparation of 3-methyl-4-(6-methyl-3,4,5-trioxo-2H,3H,4H,5H-pyridazinyl)benzoic acid

(a) Preparation of 3-methyl-4-[N'-(2-ethoxycarbonyl-1-acetyl-ethylidene)hydrazino] benzoic acid A mixture of 3 g. (19.8 mmol) of 4-amino-3-methylbenzoic acid in 50 ml. of water and 50 ml. of ethanol and 3.56 ml. of concentrated hydrochloric acid was cooled in an ice bath and then 1.5 g. of $NaNO_2$ (21.8 mmol.) in 10 ml. of water was added portionwise. The mixture was allowed to come to room temperature and then added to a solution of 4.06 g. (21.8 mmol.) of ethyl 3-acetyl-4-oxopentanoate and 8 ml. of pyridine in 25 ml. of ethanol. The reaction mixture was left for 24 hours at room temperature with stirring. The mixture was acidified with concentrated hydrochloric acid and diluted with 20 ml. of water. The resulting solid was collected and washed with water and pentane to yield 5.2 g.

(b) Preparation of 3-methyl-4-(3-acetyl-5-oxo-2-pyrazolin-1-yl)benzoic acid To a solution of a 5 g. (34 mmoles) of 3-methyl-4-[N'-(2-ethoxycarbonyl-1-acetylethylidene)hydrazino]benzoic acid in 25 ml. of ethanol and 25 ml. of water was added with stirring 34.3 ml. of a 1M sodium carbonate solution. The mixture was stirred at room temperature for 24 hours. The resulting mixture was acidified to pH 3 with 6M hydrochloric acid and the resulting solid was collected by filtration, washed with water and dried. The 3-methyl-4-(3-acetyl-5-oxo-2-pyrazolin-1-yl)benzoic acid has a melting point of >250° C.

(c) Preparation of 2-(4-carboxy-2-methylphenyl) 2,3,4,5-tetrahydro-6-methyl-pyridazine-3,4,5-trione A solution of 3 g (11 mmoles) of 3-methyl-4-(3-acetyl-5-oxo-2-pyrazdin-1-yl)benzoic acid and 8.9 g. (55 mmoles) of $FeCl_3$ in 100 ml of acetic acid was heated to reflux for 12 hours. The solution was concentrated to dryness under vacuum. The residual solid was suspended in water and then triethylamine was added until a solution resulted. The excess triethylamine was removed in vacuo and to the solution was added 4.3 g. (55 mmoles) of sodium sulfide and the mixture stirred at room temperature for 5 hours. The suspended solid was removed by filtration through celite and the filtrate was acidified with 6N hydrochloric acid. The resulting mixture was centrifuged and the supernatant liquid was discarded. The solid was resuspended and the mixture recentrifuged. Process was repeated a third time and finally the suspended solid filtered through a sintered glass funnel and washed repeatedly with water and dried to give 2.8 g. of dark solid.

EXAMPLE 2

Preparation of the Sodium Salt of 3-methyl-4-(6-methyl-3,4,5,-trioxo-2H,3H,4H,5H-pyridazinyl) benzoic acid The sodium salt of 3-methyl-4-(6-methyl-3,4,5,-trioxo-2H,3H,4H,5H-pyridazinyl)benzoic acid was prepared as follows. Six hundred mg. of 3-methyl-4-(6-methyl-3,4,5,-trioxo-2H,3H,4H,5H-pyridazinyl)benzoic acid was dissolved in 10 ml. of water/methanol, and to the solution was added excess triethylamine. The excess triethylamine was removed in vacuo and the solution passed through a 12 cm×1 cm column packed with BioRad AG 50 W-X8 resin, sodium form, and eluted with 3/1 water/methanol. The eluent was concentrated to dryness and the solid dried to give 501 mg. of dark solid.

EXAMPLE 3

Preparation of 2-chloro-4-(6-methyl-3,4,5-trioxo-2H,3H,4H,5H-pyridazinyl)benzoic acid

(a) Preparation of 2-chloro-4-[N'-(2-ethoxylcarbonyl-1-acetylethylidene)hydrazino] benzoic acid To a suspension of 1 gm. (5.8 mmoles) of 3-amino-4-chlorobenzoic acid in 20 ml. of ethanol was added 5 ml. of water and 1 ml. of 12 N hydrochloric acid. The resultant solution was cooled in an ice bath and to the cooled solution was added in small portions 442 mg. (6.4 mmoles) of sodium nitrite in 3 ml. of water. The mixture was allowed to warm to room temperature and after 30 minutes was added to a suspension of 1.19 gm. (6.4 mmole) of ethyl 3-acetyl-4-oxopentanoate, 1.8 gm. of sodium acetate, 20 ml. of ethanol and 5 ml. of water. The reaction mixture turned dark orange. After stirring for one hour, the mixture was acidified with 3N hydrochloric acid and the resultant solids collected by filtration. After drying the material, 2.53 g. was obtained.

(b) Preparation of 2-chloro-4-(3-acetyl-5-oxo-2-pyrazolin-1-yl)benzoic acid To a suspension of 1.9 gm. (5.8 mmoles) of 2-chloro-4-[N'-(2-ethoxycarbonyl-1-acetylethylidene)hydrazino] benzoic acid in 20 ml of ethanol was added at room temperature 6 ml. of aqueous 1M sodium carbonate. The mixture was left at room temperature overnight. The resulting mixture was acidifed to pH 3 with 6M hydrochloric acid and the resulting solid collected by filtration and dried. The 2-chloro-4-(3-acetyl-5-oxo-2-pyrazolin-1-yl)benzoic acid had a melting point of >250° C.

(c) Preparation of 2-(3-carboxyl-4-chlorophenyl) 2,3,4,5-tetrahydro-6-methyl-pyridazine-3,4,5-trione A solution of 281 mg. (1 mmol) of 2-chloro-4-(3-acetyl-5-oxo-2-pyrazolin-1-lyl)benzoic acid and 800 mg. (5 mmoles) of ferric chloride were heated for 12 hours at 100° C. The solvent was removed in vacuo, and the residue was suspended in water and the solid filtered and washed repeatedly with water. The solid was suspended in water, the suspension made basic to pH 9 with 5% sodium hydroxide followed by 1.2 gm. of sodium sulfide and the mixture stirred for 12 hours. The mixture was filtered through filtercell and the filtrate acidified with 6N hydrochloric acid. The mixture was centrifuged and the water decanted from the mixture. The solid was slurried with water and centrifuged a second time. The process was repeated a third time and the dark solid dried to give 88 mg. of material which had a melting point of >300° C.

EXAMPLE 4

Preparation of 4-(6-methyl-3,4,5-trioxo-2H,3H,4H,5H-pyridazinyl)benzene sulfonamide

(a) Preparation of 4-[N'-(2-ethoxcyarbonyl-1-acetyl ethylidene)hydrazino]benzene sulfonamide To a suspension of 10 g. (58.1 mmoles) of 4-aminobenzenesulfonamide in 50 ml of 1:1 ethanol/water was added 7.3 ml. of concentrated hydrochloric acid. To the cooled mixture was added in portions 4.41 g (63.9 mmoles) of sodium nitrite in 5 ml. of water. The mixture was allowed to come to room temperature and after 15 minutes was poured into a solution of 11.9 g. (63.9 mmoles) of ethyl-3-acetyl-4-oxopentanoate in 12.2 ml. of pyridine in 25 ml. of ethanol. An orange solid began to separate which was collected after 30 minutes by filtration. After drying, 24.3 g. of material was obtained.

(b) Preparation of 4-(3-acetyl-5-oxo-2-pyrazolin-1-yl)benzene sulfonamide

To a solution of 24 g. (58.1 mmoles) of the hydrazone prepared in Example 4(a) above in 100 ml. of ethanol was added 60 ml. of 1M sodium carbonate solution. The mixture was stirred at room temperature for 24 hours and then acidified with 6M hydrochloric acid. The resulting solid was collected by filtration, washed with ether and dried. The amount of product obtained was 3.4 g.

(c) Preparation of 4-(6-methyl-3,4,5-trioxo-2H,3H,4H,5H-pyridazinyl)benzene sulfonamide To a suspension of 1.5 g. (4.09 mmole) of 4-(3-acetyl-5-oxo-2-pyrazolin-1-yl)benzene sulfonamide in 5 ml. of acetic acid was added 1.94 g. (12 mmoles) of $FeCl_3$ and the mixture was heated to 90° C. for 12 hours. After cooling, the solids were collected by filtration and washed with water and dried. The material was then dissolved in 10 ml. of water and triethylamine and 2 g. of sodium sulfide added. After 2 hours, the mixture was acidified with 6N hydrochloric acid and the solid collected by centrifugation, there was obtained 1.1 g. of material.

EXAMPLE 5

Preparation of the Sodium Salt of 4-(6-methyl-3,4,5-trioxo-2H,3H,4H,5H-pyridazinyl)benzoic sulfonamide The sodium salt of 4-(6-methyl-3,4,5-trioxo-2H,3H,4H,5H-pyridazinyl)benzoic sulfonamide was prepared by dissolving 600 mg. of the sulfonamide in methanol and adding excess triethylamine. The excess triethylamine and methanol were removed in vacuo and the resulting solid dissolved in a mixture of 20% methanol and 80% deionized water. The solution was passed through a Bio-Rad Ag 50W-XS ion exchange resin (Na form). The eluent was collected and evaporated to dryness to yield 427 mg. of material.

EXAMPLE 6

Preparation of 2-(4-tetrazolylphenyl) 2,3,4,5-tetrahydro-6-methyl-pyridazine-3,4,5-trione

(a) Preparation of Ethyl 3-(4-(2-tetrazolyl)-phenylhydrazino)-4-oxopentanoate A solution of 1.06 gm. (6.58 mmoles) of 2-(4-aminophenyl)tetrazole in 20 ml. of ethanol and 1.18 ml. of concentrated hydrochloric acid and 10 ml. of water was cooled in an ice bath and treated dropwise with a solution of 500 mg. of sodium nitrite in 10 ml. of water. After the addition of an additional 10 ml. of water, the mixture was stirred for 25 minutes at room temperature. The mixture was then added to a solution of 1.35 gm. (7.2 mmoles) of ethyl 3-acetyl-4-oxopentanoate and 2.66 ml. of pyridine in 15 ml. of ethanol. A solid began to separate. After 1 hour, 10 ml. of 1M hydrochloric acid was added to adjust the pH to 2–3. An additional 50 ml. of water was added and the solid was collected and washed thoroughly with water and dried. 1.74 g. was obtained.

(b) Preparation of 3-acetyl-1-(4-tetrazolylphenyl)-4,4-dihydro-1H-pyrazol-5-one To a solution of 1.5 gm. (4.7 mmoles of ethyl 3-(4-(2-tetrazolyl)-phenylhydrazino)-4-oxopentanoate in 20 ml. of ethanol was added 5.22 mls. of a 1M aqueous sodium carbonate solution and the solution stirred for 12 hours at room temperature. The reaction mixture was treated with 15 ml. of 1M hydrochloric acid followed by 30 ml. of water. The resultant precipitate was collected by filtration, washed with water and hexane and dried. 1.35 g. of the intermediate product was obtained.

(c) Preparation of 2-(4-tetrazolylphenyl) 2,3,4,5-tetrahydro-6-methyl-pyridazine-3,4,5-trione A mixture of 350 mg. (1.3 mmoles) of the intermediate product prepared in Example 6(b), above, and 1.05 g. (6.5 mmoles) of $FeCl_3$ was heated to 85–90° C. for 12 hours. The mixture was concentrated to dryness and the residue suspended in water and the solid collected by filtration. The filter cake was dissolved in a mixture of 50% water and 50 methanol containing 1 ml. of triethylamine. The solution was concentrated to dryness, the solid redissolved in methanol and the solution concentrated to dryness to remove excess triethylamine; the residue was dissolved in 20 ml. of deionized water and to the solution was added 1.4 g. of sodium sulfide.$9H_2O$. The mixture was stirred for 45 minutes and filtered through celite. The celite was rinsed with water. The filtrate was acidified with 15 ml. of 1M hydrochloric and the mixture maintained under vacuum to remove the evolving hydrogen sulfide gas. The mixture was then centrifuged, the supernatant discarded and the solid resuspended in water and recentrifuged. The process was repeated three times and the solid finally dried. 128 mg. of dark brown solid was obtained.

EXAMPLE 7

Preparation of the Sodium Salt of 2-(4-tetrazolylphenyl) 2,3,4,5-tetrahydro-6-methyl-pyridazine-3,4,5-trione The sodium salt of 2-(4-tetrazolyl phenyl) 2,3,4,5-tetrahydro-6-methyl-pyridazine-3,4,5-trione was prepared in the following manner. A 600 mg. sample of the product of Example 6 was dissolved in a mixture of methanol/water (1:3) and triethylamine and then the solution was concentrated to dryness to remove excess triethylamine. The resultant solid was dissolved in a mixture of water/methanol (75/25), and the solution passed through a 12 cm×1 cm column packed with BioRad AG 50 W-X8 resin, sodium form, and eluted with 75/25 water/methanol. The eluent was concentrated to dryness and the solid dried.

Other pyridazine derivatives and their salts as exemplified in Examples 6 and 7, above can be prepared using the same general methods described therein.

EXAMPLE 8

Preparation of 5-indazolyl-2,3,4,5-tetrahydro-6-methyl-pyridazine-3,4,5-trione (a) Preparation of Ethyl 3-(5-indazolylhydrazino)-4-oxopentanoate A solution of 5-aminoindazole in 50 ml. of ethanol, 100 ml. of water and 8 ml. of 12M hydrochloric acid was cooled to 0° C. and a previously cooled solution of 3.41 g. (49.5 mmoles) of sodium nitrite in 10 ml. of water was added dropwise. After 30 minutes, the dark red mixture was added to the solution of 9.2 g, (49.5 mmoles) of ethyl 3-acetyl-4-oxopentanoate in 20 ml. of ethanol and 14.2 ml. of pyridine. The resulting mixture was stirred at 0° C. for 30 minutes and then at room temperature for an additional 30 minutes and finally the solid collected by filtration to give 11.2 g. of solid.

(b) Preparation of 3-acetyl-1-(5-indazolyl)-4,4-dihydro-1H-pyrazol-5-one

A solution of 10.37 g. (36 mmoles) of ethyl 3-(5-indazolylhydrazino)-4-oxopentanoate in 40 ml. of a 1M solution of sodium carbonate, 40 ml. of water and 40 ml. of ethanol was stirred at room temperature for 12 hours. The solution was diluted with 200 ml. of water and acidified to pH 3 with 1N hydrochloric acid. The brown solid which separated was collected to give 7.16 g. of product.

(c) Preparation of 5-indazolyl-2,3,4,5-tetrahydro-6-methyl-pyridazine-3,4,5-trione A solution of 242 mg (1 mmole) of 3-acetyl-1-(5-indazolyl)-4,4-dihydro-1H-pyrazol-5-one and 810 mg. (5 mmoles) of $FeCl_3$ in 10 ml. of acetic acid was heated to 90° C. for 12 hours. The acetic acid was removed under vacuum and 15 ml. of water was added to the residue. The solid was collected by filtration and then dissolved in 100 ml. of 1:1 methanol/water. Triethylamine was added until the solution was basic and the solution concentrated under vacuum to remove excess triethylamine. The solution was diluted to 30 ml. and the 1 g. of sodium sulfide added. After stirring for 2 hours the solid was removed by filtration through celite. The filtrate was acidified with 1N hydrochloric acid to pH 2 and the mixture centrifuged. The supernatant liquid was decanted from the mixture and the remaining solid was slurried with water and centrifuged a second time and the solid collected and dried to give 140 mg. of product.

This is a specific representative example of a compound of Formula I, above, in which Q and the carbon atoms to which it is attached represent a heterocyclic ring (pyrazole), with the bond between positions a, b of the heterocyclic ring forming a common bond with aromatic ring (Ar).

EXAMPLE 9

Preparation of 5-benzotriazolyl-2,3,4,5-tetrahydro-6-methyl-pyridazine-3,4,5-trione (a) Preparation of Ethyl 3-(5-benzotriazolylhydrazino)-4-oxopentanoate To a solution of 1.0 g. (7.45 mmoles) of 5-aminobenzotriazole in 10 ml. of ethanol, was added 10 ml. of water and 45 ml. of concentrated sulfuric acid. The solution was cooled to 0° C. and a solution of 560 mg. (8.2 mmoles) of sodium nitrite in 3 ml. of water was added dropwise. After 90 minutes at this temperature, the solution was added to a solution of 1.53 g. (8.2 mmoles) of 3-acetyl-4-oxopentanoate, 2.05 g. (22.3 mmoles) and sodium acetate in 10 ml. of ethanol and 20 ml. of water. A solid began to separate which was collected after 30 minutes to give 1.73 g. of product.

(b) Preparation of 3-acetyl-1-(5-benzotriazolyl)-4,4-dihydro-1H-pyrazol-5-one

To a suspension of 1.73 g. (5.98 mmoles) of ethyl 3-(5-benzotriazolylhydrazino)-4-oxopentanoate in 20 ml. of ethanol was added 9 ml. of 1M sodium carbonate. The solution was stirred for 12 hours and after acidification with 6N hydrochloric acid, the resulting solid was collected and dried to give 820 mg. of product.

(c) Preparation of 2-benzo-triazolyl-2,3,4,5-tetrahydro-6-methyl-pyridazine-3,4,5-trione To a solution of 485 mg (1.99 mmole) of 3-acetyl-1-(5-benzotriazolyl)-4,4-dihydro-1H-pyrazol-5-one in 5 ml. of acetic acid was added 1.61 g. (9.95 mmoles) of $FeCl_3$. The solution was heated to 90° C. for 12 hours. The solution was diluted with 50 ml. of water and the solid which separated was washed with water and dried. 170 mg. of dark solid was obtained.

This is another specific representative example of a compound of Formula I, above, in which Q and the carbon atoms to which it is attached represent a heterocyclic ring (triazole), with the bond between positions a,b of the heterocyclic ring forming a common bond with aromatic ring (Ar.)

Examples 10–12 illustrate the efficacy of compounds of the invention in inhibiting viral transcriptase activity, in inhibiting plaque formation by the influenza virus and in inhibiting cleavage of cap 1 RNA by the influenza virus.

EXAMPLE 10

Assay for Influenza A/WSN Virus Transcription

The assay for influenza A/WSN virus transcription was performed with detergent-treated purified influenza virions and 2'-O-methylated alfalfa mosaic virus RNA4 (AlMV RNA4) according to the following procedure. Duplicate reactions (50 μl in 96 well polypropylene U-bottom plates) contained 50 mM Hepes, pH 8, 50 mM potassium acetate, 5 mM dithiothreitol (DTT) , 5 mM magnesium chloride, 1% Triton N-101, 35 μM ATP, 0.3 μM CTP, 0.5 μM GTP, 1 μM UTP, 2 μCi 35S-UTP (Amersham SJ1303), 0.75 μg (15 μg/ml) purified virions, and 5 ng (0.4 nM) cap 1 AlMV RNA4. Test compounds were solubilized with 100% dimethylsulfoxide (DMSO) and were present in the reactions at 1% DMSO. The reference standard inhibitor, poly (A,G), was present at concentrations of 10, 3, 1, 0.3, and 0.1 μg/ml. Incubation was for 45 minutes at 31° C. Reactions were stopped by the addition of 150 μl of ice-cold 7% trichloracetic acid (TCA)+2% sodium pyrophosphate containing 50 μg/ml yeast tRNA. The TCA precipitates were filtered onto Millipore HATF plates pre-wetted with 200 μl of 7% TCA+2% sodium pyrophosphate without yeast tRNA. Plates were washed four times with 5% TCA+2% sodium pyrophosphate and filters were dried and coated with Wallac Meltilex A. Scintillant-backed filters were punched onto Fascol marking film, sealed and quantitated using a Wallac 1450 MicroBeta scintillation counter. Alternatively, a Molecular Dynamics Storm System was used; in this case, the filters were not backed with solid scintillant but were quantitated directly.

The results given in Table 1 were measured as the $IC_{50}$ or the concentration of drug compound required to achieve a 50% inhibition of influenza A/WSN virus transcriptase activity.

TABLE 1

| Example Number | $IC_{50}$ ($\mu$M) |
|---|---|
| 1 | 0.1 |
| 4 | 1 |
| 6 | 0.2 |

The low concentrations of drug compounds required to achieve 50% inhibition of the viral transcriptase activity indicate that the drug compounds of the invention are effective at inhibiting the influenza A/WSN virus transcription process.

EXAMPLE 11

Assay for Antiviral Activity Against Influenza A/WSN, A/Victoria and B/Lee Viruses Compounds were evaluated for antiviral activity against influenza A/WSN, A/Victoria and B/Lee viruses by plaque reduction in Madin Darby canine kidney (MDCK) cells. Duplicate monolayers of MDCK cells in 6 well plates were washed free of protein-containing media, infected with 50–100 plaque-forming units of virus (0.4 ml. volume), and incubated at 37° C. for 60 minutes. After aspiration of the virus inoculum, a 0.6% agarose overlay (3 ml.) containing Eagle minimal essential media, trypsin (8 $\mu$g/ml.), and the appropriate drug dilution (final concentration of 1% DMSO) was added to the cell monolayer. Plates were incubated at 37° C. in a humidified atmosphere of 5% $CO_2$ in air. After 48 hours, monolayers were fixed with glutaraldehyde, stained with 0.1% crystal violet and the plaques were counted. The percentage of plaque inhibition relative to the infected control (no drug) plates were calculated for each drug concentration and the 50% inhibitory concentration ($IC_{50}$) was determined.

The results given in Table 2 were measured as the $IC_{50}$ or the concentration of compound required to achieve a 50% inhibition of influenza virus plaque formation.

TABLE 2

| Example Number | $IC_{50}$ ($\mu$M) A/WSN | A/Victoria | B/Lee |
|---|---|---|---|
| 1 | 50 | 90 | >200 |
| 2 | 100 | | >200 |
| 3 | 16 | 50 | 175 |
| 4 | 8 | 8 | 35 |
| 5 | 8 | 11 | 30 |
| 6 | 1 | 2 | 40 |
| 7 | 2 | | 115 |
| 8 | 50 | | |
| 9 | 20 | | |

The plaque reduction results given in Table 2 illustrate that the compounds of the invention exhibit antiviral activity against the influenza virus by inhibiting plaque formation by the influenza A/WSN, A/Victoria and B/Lee viruses.

EXAMPLE 12

Assay for Cleavage of cap 1 AIMV RNA4 by Influenza Virus (a) Preparation of cap I RNAs containing 32P in the cap To prepare $^{32}$P-labeled cap 1 AIMV RNA4, the terminal $m^7$G of AIMV RNA4 was first removed by β-elimination (H. Fraenkel-Conrat and A. Steinschneider, *Methods in Enzymology* 12B, 243–246 (1967); S. J. Plotch, M. Bouloy and R. M. Drug, *Proc. Natl. Acad. Sci. USA,* 76, 1618–1622 (1979)). Two $\mu$g of β-eliminated RNA was then incubated for 1 hour at 37° C. in a 50 $\mu$l. reaction containing 25 mM Hepes, pH 7.5, 1 mM DTT, 20 units of guanylyltransferase enzyme (GIBCO/BRL #8024SA), 1 mM magnesium chloride, 4 $\mu$Ci of $^3$H-S-adenosylmethionine (Amersham TRK.614), and 100 $\mu$Ci of $^{32}$P-GTP (Amersham PB 10201). The RNA was phenol and chloroform-extracted, separated from unincorporated radionucleotides using a G-50 spun column, and ethanol-precipitated prior to being added to a cleavage reaction.

(b) Cleavage Assay

The cleavage reaction conditions were identical to the transcription reaction conditions except that no nucleotides were present and $^{32}$P-labeled cap 1 AIMV RNA4 was used. Cleavage reaction products were phenol and chloroform-extracted, ethanol precipitated, and resolved by electrophoresis on 20% acrylamide-6M urea gels. The reaction products were quantitated using a Molecular Dynamics Storm 840 imaging system.

The results given in Table 3 were measured as the $IC_{50}$ or the concentration of compound required to achieve a 50% inhibition of influenza virus cleavage of cap 1 RNA.

TABLE 3

| Example Number | $IC_{50}$ ($\mu$M) |
|---|---|
| 1 | 0.2 |
| 4 | 2 |

The low concentrations of compounds required to achieve 50% inhibition of the viral transcriptase activity indicate that the compounds of the invention are effective at inhibiting cleavage of cap 1 RNA by the influenza virus.

Example 13 shows the effect on cell growth produced by the anti-influenza compounds of the invention.

EXAMPLE 13

Cell Growth Assay

Effects of the pyridazine derivatives of the invention on cell growth were determined in MDCK cells in 96 well plates by a tetrazolium-based colorimetric method (R. Pauwels et al., *J. Virol. Methods,* 20, 309–321 (1988)). This assay detects the in situ reduction of 3-(4,5-dimethylthiazol-2-yl)-2,5-diphenyltetrazolium bromide (MTT) by viable cells. Approximately $1\times10^4$ cells were seeded per well and incubated with drug-containing growth media for 2–3 days (3–4 cell doublings). The drug concentration resulting in a reduction of optical density by 50% was determined.

The results given in Table 4 were measured as the $IC_{50}$ or the concentration of compound required to achieve a 50% reduction of optical density.

TABLE 4

| Example Number | $IC_{50}$ ($\mu$M) |
|---|---|
| 1 | >200 |
| 4 | >100 |

These results indicate that relatively high concentrations of the anti-viral compounds are required to achieve a 50% reduction of optical density which is a measure of cell growth or viability. The concentrations at which anti-influenza activity have been observed are much lower than the concentrations at which cell viability was effected.

Example 14 shows the tolerance of the drug compounds of the invention in animal studies using mice.

EXAMPLE 14

Acute Tolerance Assay

Compounds of the invention were administered to mice and the mice were then monitored for tolerance of the drug. The mice were monitored for adverse effects hourly during the 6 hours post-administration, and twice daily thereafter for 2 weeks. Euthanasia was administered to mordibund and distressed animals.

The mice (5/group; Swiss Webster female, 8–9 week old, 25–30 g) received a single administration of compounds of the invention by either the oral gavage (0.5 mL) or tail vein injection (0.2 mL) as shown in Table 5 below.

TABLE 5

Acute Tolerance

| Group (5 mice) | Compound/ Route of Admini- stration | Dose (mg/kg) | Volume Administered/ Animal |
|---|---|---|---|
| 1 | Cmpd. | 0 | 0.5 mL saline |
| 2 | of Ex. 2 | 21 (0.6 mg/28 g mouse) | 0.5 mL 1.3 mg/mL |
| 3 | Oral | 71 (2.0 mg/28 g mouse) | 0.5 mL 4.0 mg/mL |
| 4 | Gavage | 214 (6.0 mg/28 g mouse) | 0.5 mL 13 mg/mL |
| 5 | | 710 (20.0 mg/28 g mouse) | 0.5 mL 40 mg/mL |
| 6 | IV Injection | 0 | 0.2 mL saline |
| 7 | (tail vein) | 2 (0.06 mg/28 g mouse) | 0.2 mL 0.3 mg/mL |
| 8 | | 7 (0.2 mg/28 g mouse) | 0.2 mL 1 mg/mL |
| 9 | | 21 (0.6 mg/28 g mouse) | 0.2 mL 3 mg/mL |
| 10 | | 71 (2.0 mg/28 g mouse) | 0.2 mL 10 mg/mL |
| 11 | Cmpd. | 0 | 0.5 mL saline |
| 12 | of Ex. 5 | 21 (0.6 mg/28 g mouse) | 0.5 mL 1.3 mg/mL |
| 13 | Oral | 71 (2.0 mg/28 g mouse) | 0.5 mL 4.0 mg/mL |
| 14 | Gavage | 214 (6.0 mg/28 g mouse) | 0.5 mL 13 mg/mL |
| 15 | | 710 (20.0 mg/28 g mouse) | 0.5 mL 40 mg/mL |
| 16 | IV Injection | 0 | 0.2 mL saline |
| 17 | (tail vein) | 2 (0.06 mg/28 g mouse) | 0.2 mL 0.3 mg/mL |
| 18 | | 7 (0.2 mg/28 g mouse) | 0.2 mL 1 mg/mL |
| 19 | | 21 (0.6 mg/28 g mouse) | 0.2 mL 3 mg/mL |
| 20 | | 71 (2.0 mg/28 g mouse) | 0.2 mL 10 mg/mL |

With the exception of one mouse in group 20 which died, due to causes unrelated to administration of the compound itself, 2 hours after administration of the compound of the invention, all the other mice survived at least 16 days after administration of the compounds of the invention. These results indicate that mice have a high tolerance for the compounds of the invention.

Other compounds of the present invention that have been found to exhibit significant potency against influenza include (substituents given with reference to Formula I, above): 4-(6-methyl-3,4,5-trioxo-2H,3H,4H,5H-pyridazinyl)benzenecarboxamide ($R_1$=methyl; $R_2$=4-amidophenyl); 2-methyl-5- (6-methyl-3,4,5-trioxo-2H,3H,4H,5H-pyridazinyl)benzenesulfonamide ($R_1$=methyl; $R_2$=3-sulfonamido-4-methylphenyl); N-methyl-4-chloro-3-(6-methyl-3,4,5-trioxo-2H,3H,4H,5H-pyridazinyl) benzenesulfonamide ($R_1$=methyl; $R_2$=3-N-methylsulfonamide-6-chlorophenyl); N-methyl-4-(6-methyl-3,4,5-trioxo-2H,3H,4H,5H-pyridazinyl) benzenesulfonamide ($R_1$=methyl; $R_2$=4-N-methylphenylsulfonamido); N-phenyl-4-(6-methyl-3,4,5-trioxo-2H,3H,4H,5H-pyridazinyl)benzenesulfonamide ($R_1$=methyl; $R_2$=4-N-phenylsulfonamidophenyl); N-acetyl-4-(6-methyl-3,4,5-trioxo-2H,3H,4H,5H-pyridazinyl) benzenesulfonamide ($R_1$=methyl; $R_2$=N-acetyl sulfonamidophenyl); N-(3-pyridyl)-4-(6-methyl-3,4,5-trioxo-2H,3H,4H,5H-pyridazinyl)benzenesulfonamide ($R_1$=methyl; $R_2$=4-N-(3-pyridyl)sulfonamidophenyl); and 6-(6-methyl-3,4,5-trioxo-2H,3H,4H,5H-pyridazinyl)-1,1-dioxo-1,2-dihydro-1$\lambda^6$-benz<d>isothiazol-3-one ($R_1$=methyl; $R_2$=1,1-dioxo-1,2-dihydro-1$\lambda^6$-benz<d>isothiazol-3-one).

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A method of preventing influenza virus infection in a host susceptible to said infection, said me d comprising administering to said host a prophylactically effective amount of a compound having the formula:

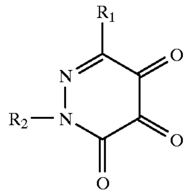

wherein $R_1$ represents a lower alkyl ($C_1$–$C_6$) substituent which may be straight or branched; $R_2$ represents an aryl substituent of the formula:

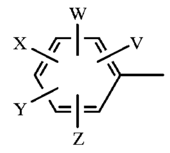 or 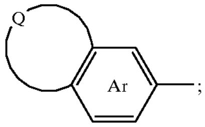;

V represents a substituent selected from the group consisting of $COOR_3$, $CONR_4R_5$, $SO_2NR_6R_7$ and

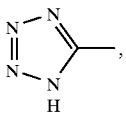, 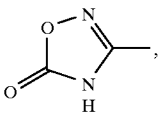, 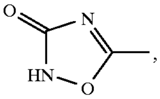,

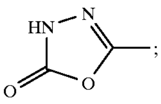;

W, X, Y and Z represent the same or different substituents selected from the group consisting of H, alkyl, halogen, $CF_3$, alkoxy, COOH, alkylthio, alkylsulfinyl, alkylsulfonyl COOR' and CONR"R'"; Q and the carbon atoms to which it is attached represent a heterocyclic ring selected from the group consisting of

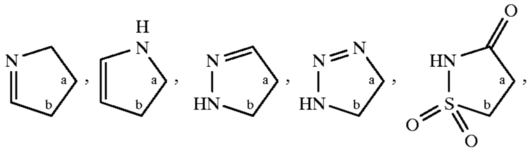

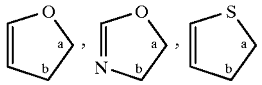

and

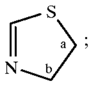

;

wherein the bond between positions a, b of said heterocyclic ring forms a common bond with aromatic ring (Ar); $R_3$, R' are the same or different and represent H or an alkyl ($C_1$–$C_6$) substituent; $R_4$, $R_5$, $R_6$, $R_7$, R" and R'" are the same or different and represent H, an alkyl substituent, an aryl substituent, an aralkyl substituent, a heterocyclic substituent, a heterocyclicalkyl substituent, an acyl substituent or a carboxyalkyl substituent, said aryl substituent and the aryl moiety of said aralkyl substituent having the formula:

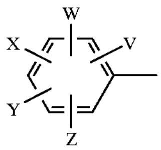

or

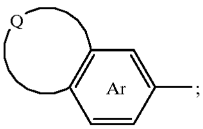

;

wherein Q, V, W, X, Y and Z are as previously defined, said heterocylic substituent or the heterocylic moiety of said heterocyclicalkyl substituent having the formula:

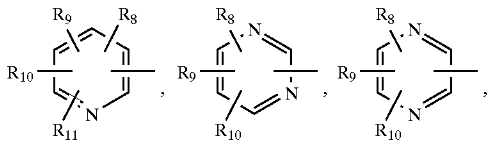

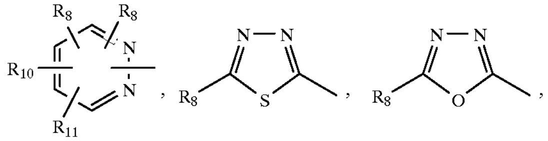

-continued

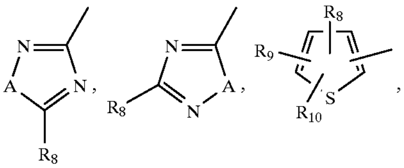

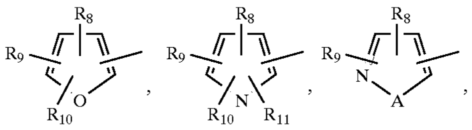

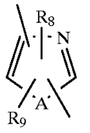

;

wherein A is selected from the group consisting of carbon, nitrogen, sulfur or oxygen, and $R_8$, $R_9$, $R_{10}$, $R_{11}$ are the same or different and represent H, alkyl, halogen, $CF_3$, alkoxy, alkylthio, OH, alkylamino, dialkylamino, COOH, $CONH_2$ and $SO_2NH_2$, and the isomers and pharmaceutically acceptable salts of said compound.

2. A method as claimed in claim 1, wherein said compound is administered in unit dosage form containing about 0.1 mg to about 50 mg of said compound per kilogram of patient body weight per day.

3. A method as claimed in claim 2, wherein said unit dosage includes a pharmaceutically acceptable carrier medium.

4. A method as claimed in claim 1, wherein said composition is administered parenterally.

5. A method as claimed in claim 1, wherein said composition is administered orally.

* * * * *